(12) United States Patent
 Mizrahy

(10) Patent No.: US 10,682,127 B2
(45) Date of Patent: Jun. 16, 2020

(54) LIGHT SOURCE AND FLUID CONDUIT ASSEMBLY

(71) Applicant: Moshe Mizrahy, Tel Aviv (IL)

(72) Inventor: Moshe Mizrahy, Tel Aviv (IL)

(73) Assignee: Inmode Ltd., Shaar Yokneam, Yokneam (IL)

( * ) Notice: Subject to any disclaimer, the term of this patent is extended or adjusted under 35 U.S.C. 154(b) by 0 days.

(21) Appl. No.: 15/963,183

(22) Filed: Apr. 26, 2018

(65) Prior Publication Data

US 2019/0328375 A1 Oct. 31, 2019

(51) Int. Cl.
| | | |
|---|---|---|
| *A61B 17/00* | (2006.01) | |
| *A61B 1/015* | (2006.01) | |
| *A61B 1/04* | (2006.01) | |
| *A61B 1/06* | (2006.01) | |
| *A61B 1/313* | (2006.01) | |
| *G03B 15/03* | (2006.01) | |
| *G03B 15/14* | (2006.01) | |

(52) U.S. Cl.
CPC ........ *A61B 17/00234* (2013.01); *A61B 1/015* (2013.01); *A61B 1/04* (2013.01); *A61B 1/0607* (2013.01); *A61B 1/3132* (2013.01); *G03B 15/03* (2013.01); *G03B 15/14* (2013.01); *A61B 2017/00283* (2013.01); *A61B 2217/007* (2013.01); *G03B 2215/0567* (2013.01); *G03B 2215/0582* (2013.01); *G03B 2215/0592* (2013.01)

(58) Field of Classification Search
CPC ..... A61B 17/00234; A61B 1/015; A61B 1/04; A61B 1/0607; A61B 1/3132; A61B 2017/00283; A61B 2217/007; G03B 15/03; G03B 15/04; G03B 2215/0567; G03B 2215/0582; G03B 2215/0592
USPC ................ 600/411, 165, 247, 249
See application file for complete search history.

(56) References Cited

U.S. PATENT DOCUMENTS

| | | | | |
|---|---|---|---|---|
| 6,322,500 | B1 * | 11/2001 | Sikora ................ | A61B 17/0206 600/219 |
| 2005/0154262 | A1 | 7/2005 | Banik | |
| 2006/0173244 | A1 | 8/2006 | Boulais | |
| 2011/0306832 | A1 | 12/2011 | Bassan | |
| 2012/0065469 | A1 * | 3/2012 | Allyn .................. | A61B 1/0676 600/109 |
| 2013/0144186 | A1 * | 6/2013 | Furlong ................ | A61B 1/018 600/563 |
| 2015/0099932 | A1 * | 4/2015 | Morimoto .......... | H05B 33/0854 600/180 |
| 2018/0035879 | A1 * | 2/2018 | Kumar ................ | A61B 1/0607 |

(Continued)

OTHER PUBLICATIONS

PCT Written Opinion and Search Report PCT/IB2019/052893, dated Aug. 1, 2019.

*Primary Examiner* — Pedro Philogene
(74) *Attorney, Agent, or Firm* — Dekel Patent Ltd.; David Klein

(57) ABSTRACT

A light source assembly (10) includes one or more lights (12) mounted on a substrate (14). A transparent cover (18) covers the one or more lights (12). A shaft (22) is coupled to the substrate (14) and to a handle (24). An electrical wire (30) is connected to the one or more lights (12) and passes through the shaft (22). A fluid conduit (32) passes through the shaft (22) and is in fluid communication with a fluid port (34) near or on the substrate (14).

5 Claims, 1 Drawing Sheet

(56) References Cited

U.S. PATENT DOCUMENTS

2018/0084986 A1\* 3/2018 Ochi ................ A61M 5/32
2018/0110406 A1\* 4/2018 Sarnaik ............ A61B 1/00087

\* cited by examiner

LIGHT SOURCE AND FLUID CONDUIT ASSEMBLY

FIELD OF THE INVENTION

The present invention relates generally to light sources, and particularly to a light source used to illuminate inner body cavities and the like during surgical procedures, such as laparoscopic procedures, and which may also have a fluid conduit for introducing a fluid for the procedure.

BACKGROUND OF THE INVENTION

There are prior art laparoscopes that contain light tubes or optical fibers, which are assembled on the laparoscope and which project light from an annulus about an object lens at the end of the laparoscope. The user can look through the sight tube of the laparoscope to inspect parts inside a body cavity illuminated by the light issuing from the laparoscope. A disadvantage is that the light source does not illuminate the entire cavity but rather only the area viewed by the sight tube of the laparoscope. Separate handheld light sources may be used together with the laparoscope in an effort to illuminate a larger area, but this has the disadvantage of requiring another person to hold the light source, or even worse, the surgeon must hold the light source in one hand and the surgical tool in the other hand, which impedes the ability of the surgeon to carry out the surgical procedure.

SUMMARY OF THE INVENTION

The present invention seeks to provide an improved laparoscopic light source for illuminating inner body cavities and the like during surgical procedures, as described more in detail hereinbelow. The light source may be used to illuminate inner body cavities and the like during surgical procedures, such as laparoscopic procedures, and may also have a fluid conduit for introducing a fluid for the procedure.

The invention is not limited to use with laparoscopes, but instead has uses with other surgical devices requiring light sources.

There is thus provided in accordance with an embodiment of the present invention an assembly including a light source assembly including one or more lights mounted on a substrate, a transparent cover covering the one or more lights, a shaft coupled to the substrate and to a handle, an electrical wire connected to the one or more lights that passes through the shaft, and a fluid conduit that passes through the shaft which is in fluid communication with a fluid port near or on the substrate.

In accordance with an embodiment of the present invention a camera is mounted near the one or more lights.

In accordance with an embodiment of the present invention the transparent cover provides positive magnification, or alternatively, negative magnification, or alternatively, different refractive or reflective effects.

In accordance with an embodiment of the present invention the shaft passes through one or more fasteners, one of the fasteners being a tightening fastener.

In accordance with an embodiment of the present invention the transparent cover covers the camera and the substrate.

In accordance with an embodiment of the present invention the camera is mounted at or near a center of the substrate and the one or more lights are mounted around the camera.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figures 1, 2:
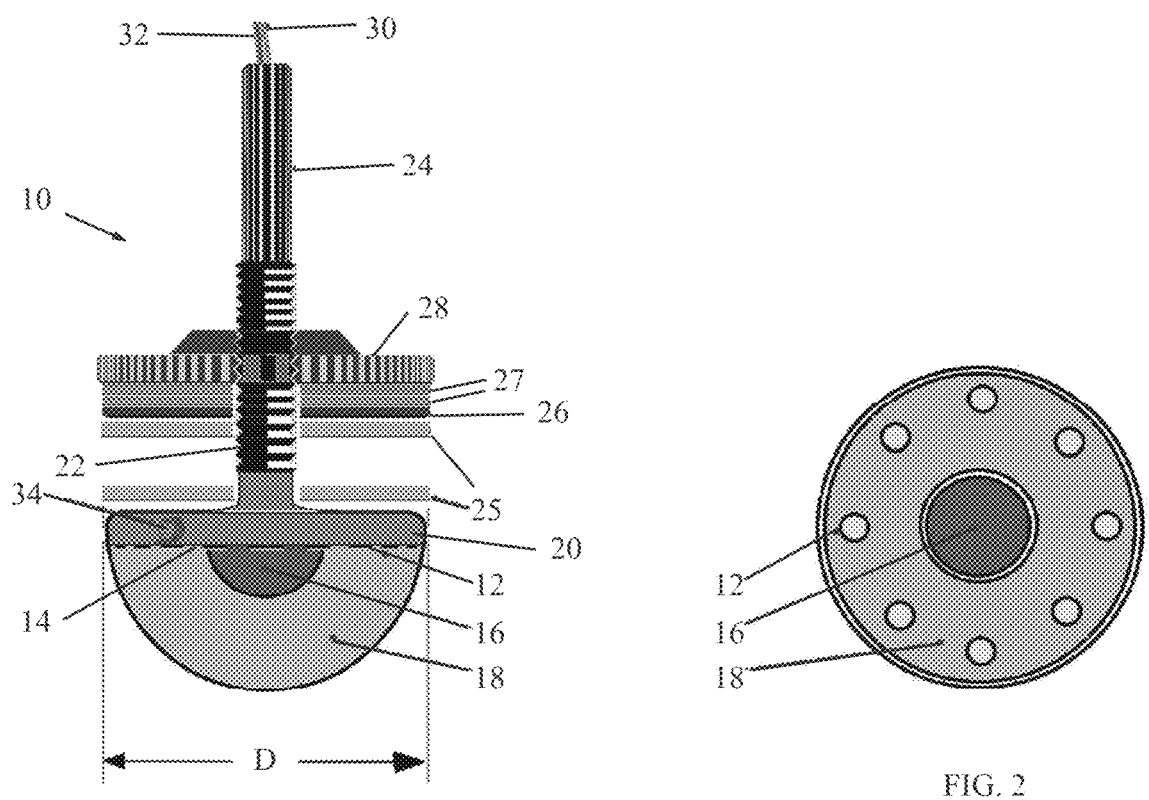
FIG. 1 is a simplified plan-view illustration of a light source assembly, constructed and operative in accordance with an embodiment of the present invention.
FIG. 2 is a simplified illustration view of the underside of the light source.

Reference is now made to FIGS. 1-2, which illustrate a light source assembly 10, constructed and operative in accordance with a non-limiting embodiment of the present invention.

Light source assembly 10 may include one or more lights 12, such as but not limited to, LEDs (light emitting diodes) of any illumination intensity and color. Lights 12 may be mounted on a substrate 14. Light source assembly 10 may optionally include a camera 16, which may be mounted near lights 12, such as on substrate 14. For example, as seen in FIG. 2, camera 16 may be mounted at or near the center of substrate 14 and lights 12 may be mounted around camera 16 near the periphery of substrate 14. Lights 12 may be symmetrically mounted around camera 14. Alternatively, lights 12 may be asymmetrically mounted around camera 14. Alternatively, lights 12 may be mounted not around camera 14, but in line with camera 14 or randomly with respect to camera 14 or at a distance from camera 14 on a different mounting surface.

A transparent cover 18 may cover lights 12, substrate 14 and camera 16. Cover 18 may have optical properties, such as to provide positive or negative magnification or different refractive or reflective effects.

A rear cover 20 may be affixed to substrate 14; alternatively, substrate 14 may serve as the rear cover. A distal portion of a shaft 22 extends proximally from rear cover 20 (or substrate 14) and a proximal portion of shaft 22 is coupled with a handle 24. Shaft 22 may be flexible or rigid. Shaft 22 may pass through one or more fasteners, such as but not limited to, a pair of axially spaced soft washers 25 (which may be made of an elastomeric material, cloth, felt, plastic and the like), a rigid washer 26 (which may be made of metal, plastic or other suitable material), one or more non-conducting washers 27 (which may be made of polytetrafluoroethylene (PTFE) or other suitable material) and a tightening fastener (e.g., nut) 28.

An electrical wire or wire harness 30 may pass through handle 24 and shaft 22 to provide electrical power to lights 12.

A fluid (i.e., gas or liquid) conduit 32 may pass through handle 24 and shaft 22 and be in fluid communication with a fluid port 34 on rear cover 20 (or substrate 14). The proximal end of fluid conduit 32 may be connected to a fluid source (not shown), such as nut not limited to, a pressurized air or other gas source, water source, saline source and others.

The diameter D of the entire assembly may be, without limitation, a few millimeters, 10 mm, 20 mm, 30 mm, 40 mm or other suitable sizes.

In use, the user makes an incision in the body (such as near the abdomen) of sufficient size to introduce the proximal portion of the light source assembly 10 therethrough, the proximal portion including the cover 18, camera 16, lights 12 and substrate 14 (and rear cover 20). The distal soft washer 25 also passes through the incision into the body cavity. The remaining fasteners are on the outside of the body so that tightening the tightening nut 28 secures the light source assembly 10 onto the patient's body and the patient's skin is sandwiched between the two soft washers 25. The lights 12 illuminate the inner body cavity and fluid may be introduced through fluid conduit 32 and out fluid port 34. Alternatively, fluids may be sucked out of the body cavity through fluid port 34 and flow through fluid conduit 32 (connected to a suction source). The light source assembly 10 thus eliminates the drawbacks of the prior art and provides illumination and fluid flow while at the same time allowing the surgeon to use both hands for the surgical procedure.

What is claimed is:

1. A method for illuminating a surgical area, comprising:
  employing a light source assembly comprising one or more lights mounted on a substrate; a transparent cover covering said one or more lights; a shaft coupled to said substrate and to a handle; an electrical wire connected to said one or more lights that passes through said shaft; a fluid conduit that passes through said shaft which is in fluid communication with a fluid port near or on said substrate; and a camera mounted near said one or more lights; and a rear cover affixed to said substrate;
  wherein a pair of axially spaced first washers and a second washer are disposed on said shaft, said first washers being softer than said second washer, and wherein a tightening fastener is threaded on said shaft, and wherein one of said first washers is a distal washer sized to completely cover said rear cover;
  making an incision in a body of sufficient size and introducing through said incision into the body, into an inner body cavity, a portion of said light source assembly, said portion including said transparent cover, said camera, said one or more lights, said substrate and said distal washer;
  securing said light source assembly to said body by positioning said distal washer on said shaft between said rear cover and an internal surface of said body and positioning another one of said first washers, said second washer and said tightening fastener on said shaft outside said body and tightening said tightening fastener such that said tightening fastener secures said light source assembly onto said body and skin of said body is sandwiched between said distal washer and said other one of said first washers; and
  illuminating said inner body cavity with said one or more lights.

2. The method according to claim 1, further comprising causing fluid to flow via said fluid conduit and said fluid port.

3. The method according to claim 2, comprising causing the fluid to flow through said fluid conduit and out said fluid port.

4. The method according to claim 2, comprising causing the fluid to flow through said fluid port and out said fluid conduit.

5. The method according to claim 2, wherein securing said light source assembly to said body comprises tightening fasteners on opposite sides of skin of said body.

* * * * *